United States Patent [19]

Hada et al.

[11] Patent Number: 4,472,738

[45] Date of Patent: Sep. 18, 1984

[54] PATTERN TESTING APPARATUS

[75] Inventors: Kazunari Hada, Kawasaki; Norio Fujii, Urawa; Atsushi Kawahara, Kawasaki; Toru Azuma, Tokyo; Junji Hazama, Kawasaki, all of Japan

[73] Assignee: Nippon Kogaku K.K., Tokyo, Japan

[21] Appl. No.: 381,469

[22] Filed: May 24, 1982

[30] Foreign Application Priority Data

May 30, 1981 [JP] Japan .................................. 56-83373

[51] Int. Cl.³ ............................................. H04N 7/18
[52] U.S. Cl. .................................... 358/106; 358/101; 358/126; 356/237
[58] Field of Search ................. 358/106, 101, 107, 96, 358/126, 165; 356/237, 239, 240, 138, 152

[56] References Cited

U.S. PATENT DOCUMENTS 4,124,865 11/1978 Zwirn .................................. 358/126
4,319,269 3/1982 Kajiura ................................ 358/126
4,353,087 10/1982 Berry et al. ......................... 358/101
4,364,089 12/1982 Woolfson ............................. 358/126
4,380,025 4/1983 Deane .................................. 358/106

*Primary Examiner*—Howard W. Britton
*Assistant Examiner*—Edward L. Coles
*Attorney, Agent, or Firm*—Fitzpatrick, Cella, Harper & Scinto

[57] ABSTRACT

A pattern defect testing apparatus comprises a first detection circuit which defines a first detection area on a two-dimensional pattern and produces a first detection signal when all digital signals representative of densities of picture cells in the first detection area have the same logical value, a second detection circuit which defines a second detection area on the two-dimensional pattern and produces a second detection signal when at least one of digital signals representative of densities of picture cells in the second detection area has a logical value different from that of the digital signals to the first detection circuit, and a discriminating circuit for discriminating the presence of a defect in the second detection area when the first and second detection signals are produced.

2 Claims, 21 Drawing Figures

FIG. 2
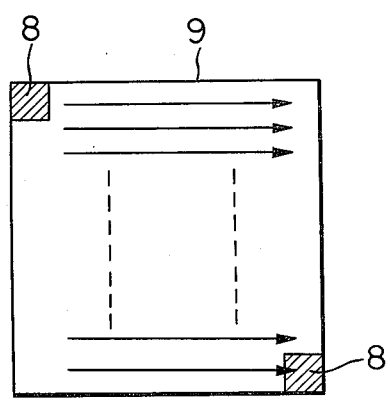
FIG. 3
FIG. 4A FIG. 4B FIG. 4C
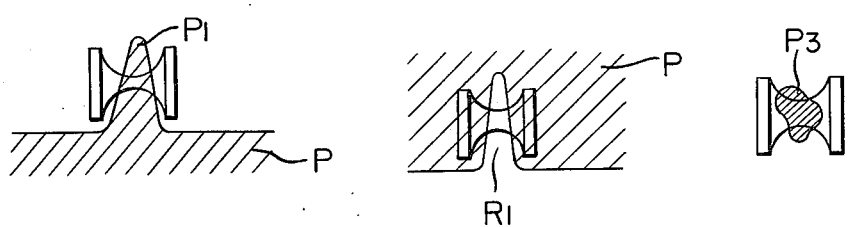
FIG. 5A
FIG. 5B
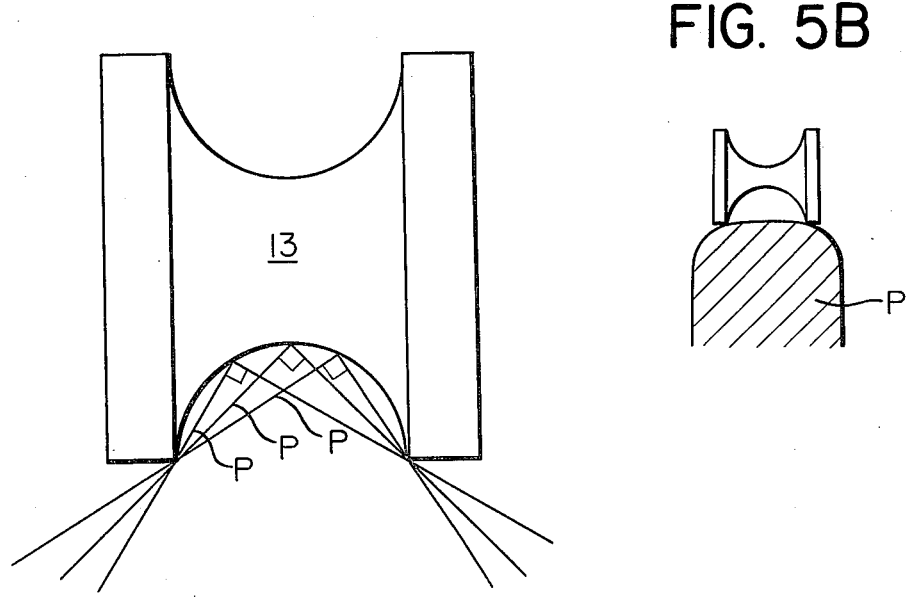

FIG. 9
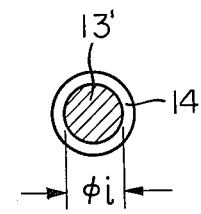
FIG. 10
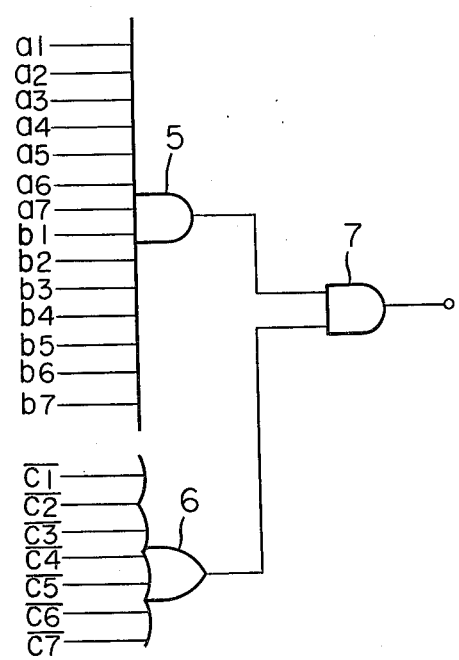
FIG. 11

PATTERN TESTING APPARATUS

BACKGROUND OF THE INVENTION

1. Field of the Invention

The present invention relates to a pattern testing apparatus which tests a digitized video signal derived from an image of a two-dimensional pattern such as a mask or a reticle used in the IC manufacture, with respect to a design pattern to detect a defect.

2. Description of the Prior Art

Prior art pattern testing apparatus which converts a two-dimensional pattern such as a mask or a reticle used in the IC manufacture to an analog video signal by an imaging device and tests the two-dimensional pattern based on a digitized video signal derived from the analog video signal uses one of the following methods:

(1) Two digitized video signals derived by imaging two adjacent chips are compared.

(2) A digitized video signal derived by imaging a pattern under test is compared with a design value.

(3) If a pattern under test has a characteristic which is not included in characteristics of a design pattern (pattern width, pattern angle, etc.), a defect is detected.

In the method (1) above, if the adjacent chips have a common defect, such a defect cannot be detected. Accordingly, a perfect detection of defect cannot be attained unless a normal chip is first selected and other chips are compared with the selected normal chip.

In the method (2) above, a huge volume of data must be stored in order to compare the pattern under test with the design value for each picture cell. In addition, due to misregistration between the design value and the pattern under test, only a defect which is larger than a certain area can be detected.

The method (3) above is relevant to the present invention. It utilizes a feature that a pattern width and a pattern-to-pattern interval of a pattern printed on the mask or reticle are always wider than a design width or a width of a pattern rule and an angle between patterns is constant. If the pattern under test has a narrower pattern than the width of the pattern rule or an angle which is not found in the pattern rule, a defect is detected. Since this method relies only on the characteristics of the pattern, no registration is required and a discrete defect which is smaller than the width of the pattern rule and a defect having a smaller pattern than the width of the pattern rule can be detected with a high precision by a simple logic circuit. However, even in the method (3) above, a special portion of a normal pattern such as an end of a right angle edge having a slope of 45 degrees may be misjudged as a defect.

SUMMARY OF THE INVENTION

It is an object of the present invention to provide a pattern testing apparatus which can exactly detect a defect in a two-dimensional pattern such as a mask or reticle.

It is another object of the present invention to provide a pattern testing apparatus which does not misjudge a special portion of a normal pattern as a defect.

In accordance with the pattern testing apparatus of the present invention, a first area and a second area are defined on the two-dimensional pattern, and means is provided for receiving digital signals one for each of the picture cells of the first and second areas and discriminating the presence of a defect in the second area when it detects that all of the picture cells of the first area have the same logical value and at least one of the picture cells of the second area has a logical value different from the logical value of the picture cells of the first area. The second area is generally rectangular shape having two opposing sides of a first length which is shorter than a width of a pattern rule and two opposing sides having a second length which is longer than the first length with at least one of the two opposing sides of the first length being concaved by at no smaller than one-half of the first length, and the first area has two equal sub-areas adjacent to the two opposing sides of the second length of the second area to sandwitch the second area are defined on the two-dimensional pattern. The concave area is defined by an arc of a circle having a diameter equal to the first length and a chord having a length equal to the first length.

BRIEF DESCRIPTION OF THE DRAWINGS

FIG. 2 shows a chart for explaining a portion of operation of the present invention, FIG. 3 shows a detection area defined by a template in accordance with the present invention, FIGS. 4A to 4C and 5A to 5B show charts for explaining other portions of the operation of the present invention, FIGS. 6A to 6C, 10 and 11 show various detection areas used in the present invention, FIGS. 7A to 7D show windows and templates corresponding to the detection area shown in FIG. 3, FIG. 8 shows one embodiment of a circuit for the template shown in FIG. 7A, FIG. 9 shows a template corresponding to the detection area shown in FIG. 6C, FIG. 10 shows an embodiment of a circuit for the template shown in FIG. 9.

DETAILED DESCRIPTION OF THE PREFERRED EMBODIMENTS

Figure 1:
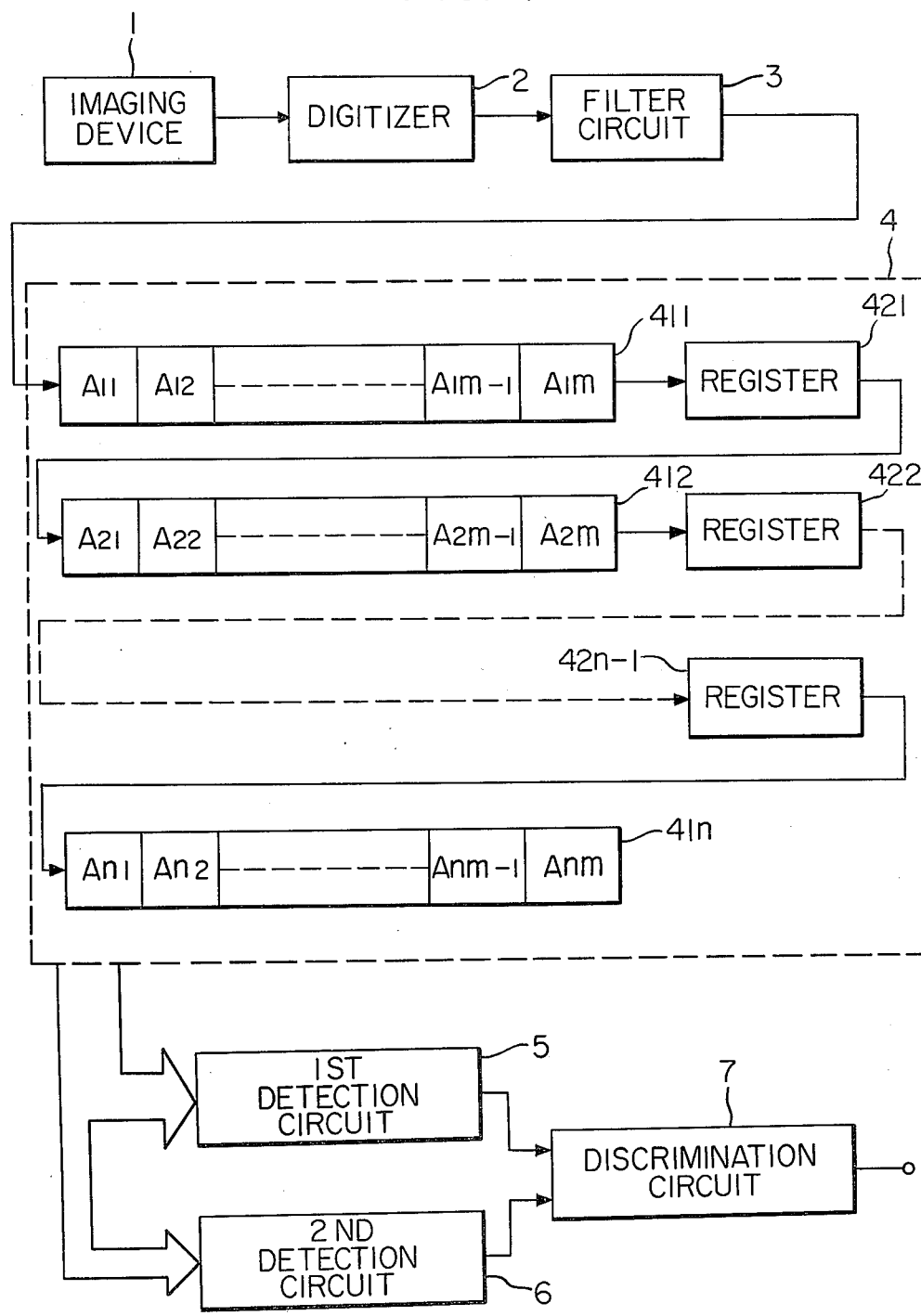
FIG. 1 shows a block diagram of a configuration of a pattern testing apparatus of the present invention.

FIG. 1 shows a block diagram of a configuration of the present invention. A two-dimensional pattern such as a mask or a reticle in the IC manufacture is converted to an analog video signal representing a density of the pattern by an imaging device 1, and the analog video signal is converted by a digitizer 2 to a two-valued digital signal in synchronism with a clock pulse generated by a clock pulse generator, not shown. A filter circuit or smoothing circuit 3 eliminates a noise component included in the digital signal and supplies the digital signal to a set of shift registers 4 in synchronism with the clock pulse. The shift registers 4 sequentially store and shift the digital signal in the form of two logical values represented by two signals in synchronism with the clock pulse. The shift registers 4 comprise n registers 411, 412, . . . 41n and n−1 registers 421, 422, . . . 42n−1. The sums of the registers 411 and 421, 412, and 422, . . . ,41n−1 and 42n−1, respectively, are equal to the number of picture cells in one horizontal scan line of the imaging device 1. The shift registers 411, 412, . . . 41n have m bit positions $A_{11}, A_{12} \ldots A_{1m}; A_{21}, A_{22}, \ldots A_{2n}; \ldots; A_{n1}, A_{n2}, \ldots A_{nm}$, respectively.

Hatched areas shown in FIG. 2 are windows 8 each of which comprises nxm picture cells loaded to the shift registers 411, 412, ... 41n from the reticle or pattern 9.

A first detection circuits 5 and a second detection circuit 6 sequentially receive the digital signal corresponding to the picture cells to be detected which are in the window 8, from the shift registers 411, 412, ... 41n in synchronism with the clock pulse. The picture cells to be detected by the first detection circuit 5 and the second detection circuit 6, respectively, are called templates.

Referring to FIG. 3, detection areas 11 and 12 are defined by the template associated with the first detection circuit 5, and a detection area 13 is defined by the template associated with the second detection circuit 6. The first detection circuit 5 and the second detection circuit 6 receive the digital signals representing the density of the picture cells in the corresponding templates and supply detection signals to a discrimination circuit 7, which checks any defect in the area based on the detection signal.

Referring to FIG. 3, of the detection areas defined by the templates in the window 8 associated with the first detection circuit 5 and the second detection circuit 6, the detection areas 11 and 12 correspond to the template associated with the first detection circuit 5 and the detection area 13 corresponds to the template associated with the second detection circuit 6. A template inner width $\phi i$, a template length l and a template radius r have the following relations.

$$\phi i < W_0 - \omega$$

$$r = \phi i/2$$

$$l > 2r + 2\delta$$

where $W_0$ is a pattern rule width, $\omega$ is a thinning/thickening factor of the pattern in pre-processing by the digitizer 2 and the filter circuit 3 (the template inner width $\phi i$ is always narrower than the pattern rule width $W_0$ in the window 8), and $\delta$ is a width permitted for roundness of a corner of the pattern per se, roundness of the corner of the pattern due to the pre-processing, and irregularity of pattern boundary. A concaved area defined by an arc having a radius r is formed in the detection area 13 to prevent misdetection of a normal pattern as a defect, as will be explained later with reference to FIGS. 5A and 5B. The shapes and the sizes of the detection areas 11, 12 and 13 are defined in this manner, and logical values for the picture cells forming the detection areas 11, 12 and 13 are defined as follows:

$$ai(i=1\sim k)$$

$$bj(j=1\sim k)$$

$$ck(k=1\sim l)$$

It is assumed that the mask or reticle pattern comprises dark areas and light areas and the dark areas are represented by logical value "1" and the light areas are represented by logical value "0". When DEFB defined by the following logical expression is "1", it is determined that a defect is in the dark area, and when DEFW defined by the following logical expression is "1", it is determined that a defect is in the light area.

$$DEFB = (\overline{a_1} \cdot \overline{b_1} \cdot \overline{a_2} \cdot \overline{b_2} \ldots \overline{a_k} \cdot \overline{b_k}) \cdot (c_1 + c_2 + \ldots c_l) \quad (1a)$$

$$DEFW = (a_1 \cdot b_1 \cdot a_2 \cdot b_2 \ldots a_k \cdot b_k) \cdot (\overline{c_1} + \overline{c_2} + \ldots \overline{c_l}) \quad (1b)$$

Both the expressions (1a) and (1b) simultaneously assume "1" when all of the logical values ai and bi representing the picture cells forming the detection areas 11 and 12 are of the same logical value and at least one of the logical values ci representing the picture cells forming the detection area 13 is different from the logical value of ai and bi. In this case, a smaller pattern than the pattern rule width $W_0$ exists and it should be regarded as a defect. In FIG. 4A, a hatched area represents the dark area and a non-hatched area represents the light area. When the dark area P has a projection $P_1$, DEFB in the expression (1a) assumes "1" and the dark area defect is detected. In FIG. 4B, if the dark area P has a recess $R_1$, DEFW in the expression (1b) assumes "1" and the light area defect is detected.

In FIG. 4C, when a dark area defect of a discrete pattern smaller than the pattern rule width $W_0$ exists, DEFB in the expression (1a) assumes "1". On the other hand, when a light area defect of a discrete recess smaller than the pattern rule width $W_0$ exists in the dark area, DEFW in the expression (1b) assumes "1". The concaved area defined by the arc of radius r in the detection area 13 may be formed on at least one side, as is apparent from FIG. 4A.

If the detection area is on a defect-free pattern, the second term of the right side of each of the expressions (1a) and (1b) is "0" when the first term thereof is "1", and the first term is "0" when the second term is "1". Accordingly, the normal design pattern is not misdetected as a defect. As shown in FIG. 5A, a pattern having a 90-degree corner can be correctly detected because the detection area 13 has the concave areas defined by the arc having the radius of $r = \phi i/2$. As shown in FIG. 5B, a round corner of the pattern can also be correctly detected.

Figure 6A:
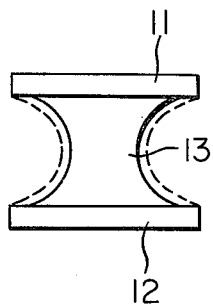
Figure 6B:
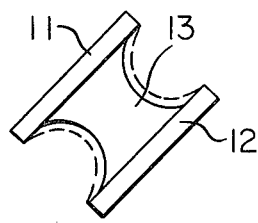
Figure 6C:
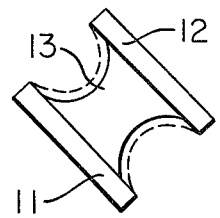

The detection area shown in FIG. 3 can mainly detect the defect having a vertical component as shown in FIGS. 4A and 4B. By providing a detection area for detecting a defect having a horizontal component as shown in FIG. 6A, a detection area for detecting a defect in a 45-degree direction as shown in FIG. 6B and a detection area for detecting a defect in a 135-degree direction as shown in FIG. 6C, the defects having horizontal, 45-degree and 135-degree components and the discrete defect can be detected. In order to detect the defects in more finely, the detection areas having 15-degree, 30-degree, 60-degree, 75-degree, 105-degree, 120-degree, 150-degree and 165-degree directivities may be provided.

When the size of the detection area is fixed, a detection sensitivity is fixed depending on the size of the defect for the defect near the boundary of the dark area and the light area. Accordingly, by providing the detection areas of various sizes and various directivities within a range which meets a condition that the template inner width $\phi i$ is narrower than $W_0 - \omega$, all of the small defects can be detected and the types of the defects such as sizes and directions can be determined.

Specific examples of the window 8 of the template are now explained. It is now assumed that the pattern rule width $W_0$ is eight picture cell length, the thinning or thickening of the pattern by the pre-processing is one picture cell length, and the roundness of the corner of the pattern and the irregularity $\delta$ of the pattern boundary are one picture cell length, respectively. Under such an assumption, the width of the mask or reticle pattern, when it is digitized, may assume 7 to 9 picture cell length. Accordingly for the vertical and horizontal directivity templates, the template inner width φi may be 2, 4, 5 and 6 picture cell length. FIGS. 7A to 7D show the templates for the vertical directivity detection area.

In FIGS. 7A to 7D, the window 8 is divided into 11×11 picture cells and the templates for defining the detection areas for detecting the vertical directivity defects are shown for the template inner width φi of 3 to 6 picture cell length. The 11×11 picture cells are defined by rows A, B, . . . K and columns 1, 2, . . . 11. In FIGS. 7A to 7D, a left line of picture cells designated by "1" correspond to the detection area 11, a right line of picture cells designated by "1" correspond to the detection area 12 and the picture cells designated by "0" correspond to the detection area 13. The picture cells designated by "1" represent the template associated with the first detection circuit 5 and the picture cells designated by "0" represent the template associated with the second detection circuit 6.

Figures 7C, 7D, 8:
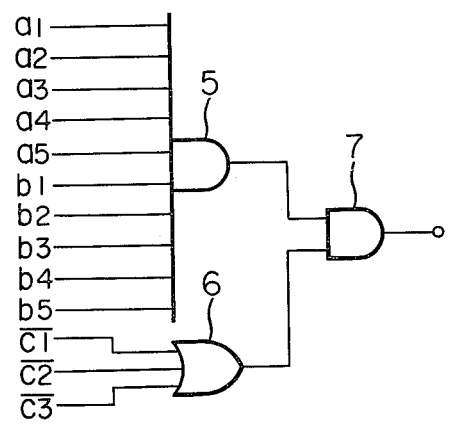

The first detection circuit 5, the second detection circuit 6 and the discrimination circuit 7 carry out the logical operations in accordance with the expressions (1a) and (1b) described above. In the detection of the defect such as the light area defect $R_1$ shown in FIG. 4B, when the template is defined as shown in FIG. 7A, the first detection circuit 5, the second detection circuit 6 and the discrimination circuit 7 are constructed as shown in FIG. 8. The logical values of the picture cells D4, E4, F4, G4 and H4 corresponding to the detection area 11 are designated by $a_1, a_2, \ldots a_5$, respectively, the logical values of the picture cells D8, E8, F8, G8 and H8 corresponding to the detection area 12 are designated by $b_1, b_2, \ldots b_5$ respectively, and the logical values of the picture cells F5, F6 and F7 corresponding to the detection area 13 are designated by $c_1, c_2$ and $c_3$, respectively. The first detection circuit 5 is an AND gate which receives the digital signals having the logical values $a_1 \sim a_5$ and $b_1 \sim b_5$, the second detection circuit 6 is an OR gate which receives the digital signals having the logical values of inversions of $c_1 \sim c_3$, and the discrimination circuit 7 is an AND gate. The second detection circuit 6 may be a NAND gate which receives the digital signals having the logical values $c_1 \sim c_3$. When the defect such as the dark area defect $P_1$ shown in FIG. 4A is detected, the first detection circuit 5 is an AND gate which receives the digital signals having the logical values of inversions of $a_1 \sim a_5$ and $b_1 \sim b_5$, the second detection circuit 6 is an OR gate which receives the digital signals having the logical values $c_1 \sim c_3$, and the discrimination circuit 7 is an AND gate, as is apparent from the expression (1a). The first detection circuit 5 may be a NOR gate which receives the digital signals having the logical values $a_1 \sim a_5$ and $b_1 \sim b_5$. The first detection circuits 5, the second detection circuits 6 and the discrimination circuits 7 for the templates shown in FIGS. 7B to 7D can be similarly constructed. The discrimination circuit 7 detects a defect in one of the picture cells, for example, the picture cell F6, in the template associated with the second detection circuit 6.

FIG. 9 shows a 135-degree directivity template corresponding to the detection area shown in FIG. 6C. The template associated with the first detection circuit 5, which is shown by the picture cells designated by "1" is defined not only by the picture cells F2, G3, H4, I5 and J6 and the picture cells B6, C7, D8, E9 and F10 having the logical values $a_1 \sim a_5$ and $b_1 \sim b_5$, respectively, but also by additional picture elements H3 and I4 and picture elements C8 and D9 having logical values of $a_6, a_7$ and $b_6, b_7$, respectively. The template associated with the second detection circuit 6, which is shown by the picture cells designated by "1" is defined by the picture cells E7, F6, G5, G4, H5, D7 and E8 having logical values $c_1 \sim c_7$, respectively. By combining the picture cells G4, H5 and D7, E8 with the diagonally adjacent picture elements H3, I4 and C8, D9 which have different logical values from those of the former, in the defect detection logic, the defect which belongs to only the detection area 13 can be detected. The first detection circuit 5, the second detection circuit 6 and the discrimination circuit 7 may be constructed as shown in FIG. 8. FIG. 10 shows an embodiment of the construction of the first detection circuit 5, the second detection circuit 6 and the discrimination circuit 7 for detecting the light area defect in the template shown in FIG. 9. A similar effect can be attained even if the picture cells G4, H5 and D7, E8 are not used in the defect detection logic.

FIG. 11 shows a detection area defined by a template for detecting a small discrete defect. A hatched area 13' is a circle having a diameter φi and a ring area 14' intersects the area 13' from an external area. The logical values of the picture cells forming the area 14' and the area 13' are defined as follows, respectively:

$$ab_i (i = 1 \sim k')$$

$$c'_k (k = 1 \sim l')$$

Thus, when DEFB' defined by the following logical expression is "1", it is determined that a discrete dark area defect exists, and when DEFW' defined by the following logical expression is "1", it is determined that a discrete light area defect exists.

$$DEFB' = (\overline{ab_1} \cdot \overline{ab_2} \ldots \overline{ab_{k'}}) \cdot (c'_1 + c'_2 + \ldots c'_{l'}) \qquad (1a')$$

$$DEFW' = (ab_1 \cdot ab_2 \cdot \ldots ab_{k'}) \cdot (\overline{c'_1} + \overline{c'_2} + \ldots \overline{c'_{l'}}) \qquad (1b')$$

Figures 12, 13:
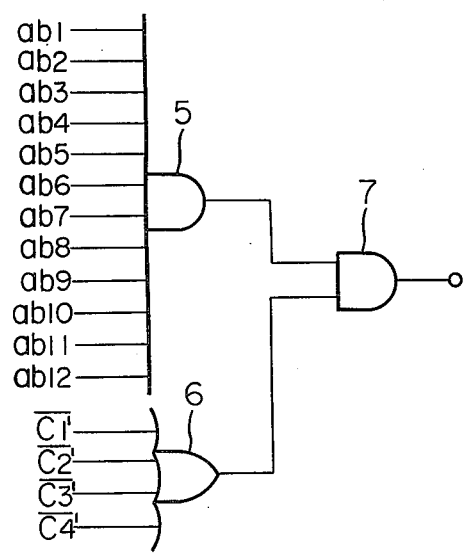
FIG. 12 shows a window and a template corresponding to the detection area shown in FIG. 11.
FIG. 13 shows an embodiment of a circuit for the template shown in FIG. 11.

FIG. 12 shows an example of the template in the window 8 corresponding to the detection area shown in FIG. 11. The template associated with the first detection circuit 5, which is shown by the picture cells designated by "1" is defined by the picture cells D6, D7, E5, E8, F4, F10, G4, G10, H5, H8, I6, and I7 having logical values $ab_1, ab_2, \ldots ab_{12}$, respectively. The template associated with the second detection circuit 6, which is shown by the picture cells designated by "0" is defined by the picture cells F6, F7, G6 and G7 having the logical values $c_1', c_2', \ldots c_4'$, respectively. The expressions (1a') and (1b') correspond to the expressions (1a) and (1b), respectively. Accordingly the first detection circuit 5, the second detection circuit 6 and the discrimination circuit 7 may be constructed as shown in FIG. 8. FIG. 13 shows an embodiment of the construction of the first detection circuit 5, the second detection circuit 6 and the discrimination circuit 7 for detecting the discrete light area defect in the template shown in FIG. 12.

We claim:

1. A two-dimensional pattern defect testing apparatus wherein digital signals representative of a two-dimensional pattern having a line pattern are serially stored in register means, said two-dimensional pattern is divided into a predetermined number of picture cells, the densities of the respective picture cells are represented by said digital signals and a defect in said two-dimensional pattern is detected based on said digital signals stored in said register means, comprising:

(a) first detection means including means for defining a first area on said two-dimensional pattern, said first detection means receiving digital signals representative of the pattern in said first area from said register means and producing a first detection signal when all of the received digital signals have the same logical value;

(b) second detection means including means for defining a second area on said two-dimensional pattern, said second detection means receiving the digital signals representative of the pattern in said second area and producing a second detection signal when at least one of the received digital signals has a logical value different from the logical value of the digital signals received by said first detection means;

said second area being within a rectangle having two opposing sides separated by a shorter distance than a width of said line pattern and being analogous to a shape defined by said two opposing sides and a pair of opposing line segments extending between opposite ends of said two opposing sides, at least one of said pair of line segments being an arc;

said first area including two areas adjacent to said two opposing sides of said second area; and (c) discrimination means for discriminating the presence of the defect in said second area when said first detection signal and said second detection signal are applied thereto.

2. A two-dimensional pattern defect testing apparatus wherein digital signals representative of a two-dimensional pattern having a line pattern are serially stored in register means, said two-dimensional pattern is divided into a predetermined number of picture cells, the densities of the respective picture cells are represented by said digital signals and a defect in said two-dimensional pattern is detected based on said digital signals stored in said register means, comprising:

(a) first detection means including means for defining a first area on said two-dimensional pattern, said first detection means receiving digital signals representative of the pattern in said first area from said register means and producing a first detection signal when all of the received digital signals have the same logical value;

(b) second detection means including means for defining a second area on said two-dimensional pattern, said second detection means receiving the digital signals representative of the pattern in said second area and producing a second detection signal when at least one of the received digital signals has a logical value different from the logical value of the digital signals received by said first detection means;

said second area being analogous to a shape defined by a circle having a shorter diameter than a width of said line pattern;

said first area being adjacent to said second area and analogous to a shape of a ring encircling said second area; and (c) discrimination means for discriminating the presence of the defect in said second area when said first detection signal and said second detection signal are applied thereto.

* * * * *

UNITED STATES PATENT AND TRADEMARK OFFICE
CERTIFICATE OF CORRECTION

PATENT NO. : 4,472,738
DATED : September 18, 1984
INVENTOR(S) : KAZUNARI HADA, ET AL.

It is certified that error appears in the above-identified patent and that said Letters Patent is hereby corrected as shown below:

Column 1, lines 9 and 14, delete "the".

Column 2, line 5, after "is" insert --of--;

line 10, "no smaller" should read --least not less--.

Column 4, line 49, delete "in".

Signed and Sealed this

Twenty-sixth Day of February 1985

[SEAL]

Attest:

DONALD J. QUIGG

Attesting Officer     Acting Commissioner of Patents and Trademarks